(12) United States Patent
Maynard (10) Patent No.: US 9,023,428 B2
(45) Date of Patent: *May 5, 2015

(54) METHOD OF DELIVERING COMPOSITIONS TO SUBSTRATES

(71) Applicant: Koppers Performance Chemicals Inc., Pittsburgh, PA (US)

(72) Inventor: Nigel P. Maynard, Waitakere (NZ)

(73) Assignee: Koppers Performance Chemicals Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/861,648

(22) Filed: Apr. 12, 2013

(65) Prior Publication Data

US 2013/0230668 A1     Sep. 5, 2013

Related U.S. Application Data

(63) Continuation of application No. 10/539,685, filed as application No. PCT/NZ03/00277 on Dec. 12, 2003, now Pat. No. 8,425,980.

(30) Foreign Application Priority Data

Dec. 16, 2002 (NZ) ........................................ 523249

(51) Int. Cl.
*A61K 9/72* (2006.01)
*B27K 3/02* (2006.01)
*B05D 3/02* (2006.01)
*B05D 7/06* (2006.01)
*B27K 5/00* (2006.01)

(52) U.S. Cl.
CPC ............ *B27K 3/0207* (2013.01); *B05D 3/0218* (2013.01); *B05D 7/06* (2013.01); *B27K 3/0285* (2013.01); *B27K 5/001* (2013.01)

(58) Field of Classification Search
USPC ......................................................... 427/317
See application file for complete search history.

(56) References Cited

U.S. PATENT DOCUMENTS

| 2,069,491 | A | 2/1937 | Hagar |
| 4,287,239 | A | 9/1981 | Hager |
| 4,325,993 | A | 4/1982 | Schroder |
| 4,343,095 | A | 8/1982 | Rosen et al. |
| 4,615,739 | A | 10/1986 | Clark et al. |

(Continued)

FOREIGN PATENT DOCUMENTS

| CA | 976813 | 10/1975 |
| JP | 10-315203 | 12/1998 |

(Continued)

OTHER PUBLICATIONS

Baileys et al., "Thermal Treatment of Western Red Cedar with Copper Naphthenate", published at www.merichem.com, Jun. 27, 2005.

*Primary Examiner* — Gordon R Baldwin
*Assistant Examiner* — Nathan T Leong
(74) *Attorney, Agent, or Firm* — Covington & Burling LLP (57) ABSTRACT

Method of delivering compositions to organic substrates, particularly lumber. Method involves heating a target zone of the substrate and then applying the composition to the surface of the substrate wherein the temperature of the composition is lower than that of the target zone of the substrate. Compositions include biocidal, strength modifiers, waterproofing and polymers.

31 Claims, 2 Drawing Sheets

(56) References Cited

U.S. PATENT DOCUMENTS

| | | |
|---|---|---|
| 4,908,392 A | 3/1990 | Kusano et al. |
| 5,447,686 A | 9/1995 | Seidner |
| 5,468,284 A | 11/1995 | Sturm |
| 5,527,579 A | 6/1996 | Aho |
| 5,555,642 A | 9/1996 | Rem et al. |
| 5,871,817 A | 2/1999 | Nasheri |
| 6,105,278 A | 8/2000 | Gerrish et al. |
| 6,187,387 B1 | 2/2001 | Bolle et al. |
| 6,235,403 B1 | 5/2001 | Vinden et al. |
| 6,248,402 B1 | 6/2001 | Guyonnet et al. |
| 6,345,450 B1 | 2/2002 | Elder |
| 6,596,975 B1 | 7/2003 | Vinden et al. |
| 2004/0258941 A1 | 12/2004 | Neogi et al. |
| 2008/0022548 A1* | 1/2008 | Maynard et al. ............... 34/396 |
| 2009/0280345 A1* | 11/2009 | Maynard et al. ............... 428/541 |

FOREIGN PATENT DOCUMENTS

| | | |
|---|---|---|
| NZ | 272276 | 12/1995 |
| WO | 01/38055 A1 | 5/2001 |
| WO | 02/00404 A1 | 1/2002 |

* cited by examiner

METHOD OF DELIVERING COMPOSITIONS TO SUBSTRATES

CROSS REFERENCE TO RELATED APPLICATION

This application is a continuation of U.S. patent application Ser. No. 10/539,685, filed Aug. 9, 2006, now issued as U.S. Pat. No. 8,425,980, which is a national phase under 35 USC 371 of international application no. PCT/NZ2003/000277, filed Dec. 12, 2003, which claims the benefit of the priority date of New Zealand Patent Application No. 523249, filed Dec. 16, 2002. The contents of the aforementioned applications are incorporated herein in their entirety.

FIELD

This invention relates to methods of delivering compositions to organic substrates. In particular, the invention relates to methods of delivering compositions to lignocellulosic substrates, such as lumber. The methods may be for the purpose of prevention of growth of pest organisms, or for providing specific properties to the substrate, for example.

BACKGROUND

There are known methods for delivering a composition to a substrate. These techniques may vary depending on the nature of the substrate to which a composition is to be applied, and whether or not the composition is required to penetrate the surface of the substrate. Many of these known methods require complex machinery and also active pressure systems which require a lot of power input. There may be a number of other disadvantages of known methods. The following background discussions outline, by way of example, techniques used to deliver compositions to lignocellulosic substrates such as freshly felled logs or processed lumber.

Lignocellulosic material, and more specifically debarked logs or sawn lumber, largely because these are of biological origin, are prone to attack by organisms such as bacteria, insects, nematodes and a variety of fungi including decay and staining fungi. Such attack reduces the service life of logs or lumber extracted therefrom, degrades the appearance of the logs or lumber, and reduces the service life of such materials with resultant cost of replacement or potential hazard due to failure.

Logs, or lumber, when freshly cut, generally are not contaminated internally by fungi. However, as soon as the wood substrate is exposed by either bark damage or by cutting, fungal spores attach to any exposed surface and begin growing by utilising the available carbohydrates and resin acids as a food source. A number of fungal species including *Ophiostoma* species are known to grow rapidly into the substrate and quickly move beyond the control of readily available fungicides. There is also a window of opportunity for pest organisms to colonise such substrates between the period of felling and the time at which pesticidal treatments are applied. This infection by pest organisms prior pesticidal treatment may be referred to as "pre-infection" and is a significant problem for the lumber industry.

To mitigate infection by biological pests methods have been developed to treat these substrates with a variety of chemicals by various physical processes. Unfortunately, these processes may be considered to have one or more disadvantages. Some such processes and their disadvantages are noted herein below.

Lignocellulosic substrates are complex structures including lumber cells interconnected by pits which include a membrane otherwise acting as a valve system when the tree is living. Such cells and cell interconnections offer impedance to the flow of preservative into the substrate. This is more particularly so when the substrate is dry because the pit membranes aspirate, that is they collapse to either side of the pit and effectively seal it shut. Drying of the substrate however is important prior to treatment with preservative because space is required within which to place the preservative. Consequently a large number of variations of vacuum/pressure processes have been developed to overcome this impedance thus allowing flow of a composition (for example a biocide or preservative composition) throughout the entire substrate to ensure total protection.

Several such processes include those of: 1) Rueping: Pre-pressure with gas followed by pressure with preservative or chemical solution; 2) Lowry: Pressure impregnation with preservative or chemical solution; and 3) Bethel: Vacuum followed by pressure impregnation with preservative or chemical solution. These processes are described in "Industrial Timber Preservation", 1979, J G Wilkinson, Associated Business Press.

The Rueping process applies pre-pressure with gas prior to treatment with preservative fluids. This pre-pressure with gas fills the cells with a compressible medium such that after treatment with fluid the gas will expand forcing out any surplus fluid. However this can result in ongoing kickback of preservative contaminated fluid which may be hazardous and which kickback fluid may contain extractives which will interfere with preservative chemistry.

The Rueping and Lowry processes retain gas within the void spaces within the substrate. Thus, the impregnation process requires pumps to force fluid into the substrate against the back pressure of the gases in the voids.

The Bethel process removes all gases from the cells by application of a vacuum which cells then become completely filled with preservative fluid. This method has the disadvantage that lumber is completely filled with aqueous fluid which can not be sucked out again. Accordingly, the lumber takes considerable time to dry.

It is noted that some of these processes necessitate impregnation of up to 700 liters of chemical solution per cubic meter of lumber, in for example softwoods.

These systems also have the disadvantage that preservative or chemical composition is recycled back and forth between the pressure vessel and the storage tanks. This can lead to contamination of the solution by lumber extractives. This can cause problems. For example, in cases where preservatives contain hexavalent chromium, lumber extractives in the preservative composition may cause a chemical imbalance. Recycling of compositions can also be a problem where ammoniacal preservatives are used because ammonia can volatilise causing precipitation of other components resulting in hazardous emissions. Use of alternative chemicals which are not necessarily preservatives also suffer from these problems.

There are examples of processes which attempt to alter the properties of some substrates such as lumber by impregnation with polymeric materials. Plant and equipment for such processes is very expensive. Large steel pressure vessels are required which must sustain positive pressures of 600 pounds per square inch, or vacuum of nearly minus 15 pounds per square inch. To assist these processes it is necessary to have large, high volume, high pressure pumps and, high volume, high vacuum pumps. Not only are these expensive, they must operate in quite corrosive chemical environments, which leads to costly repair and maintenance. Since the treatment plant is large and the pressure vessel may have a capacity of 30 cubic meters, it is necessary to have similar sized storage vessels to contain the operating fluid. Due to the size of the plant equipment and the risk of preservative spillage it is necessary to house the plant in a contained building. Accordingly, this type of facility is very capital expensive to build and operate.

A critical issue of all the above processes is the size of the operation and more significantly the need to store large volumes of hazardous chemicals.

Various other methods have been developed to treat lumber with various compositions. For example: U.S. Pat. No. 3,964,863 describes a method which uses a pressure vessel for treatment of lumber in which the pressure of the impregnating fluid is increased isostatically in a controlled manner causing the impregnating fluid to be distributed throughout substantially all of the material; U.S. Pat. No. 4,303,705 describes a method of treatment of lumber with water-borne preservatives, such as CCA salts, in which the preservatives are forced into the lumber under pressure and the water-borne lumber treatment materials are held within the lumber under pressure until they are deposited as by precipitation or chemical affixation; and, U.S. Pat. No. 4,433,031 describes a method of impregnating lumber with a preservative wherein the treatment is carried out by exposing the lumber, while submerged in the treating solution, to one or more cycles of reduced pressure (i.e. vacuum) and elevated pressure.

Additional examples include: U.S. Pat. No. 4,466,998 which describes the use of water-borne preservatives to impregnate lumber by the empty-cell pressure impregnation method without the precipitation of water-borne salts such as chromium, copper and arsenic when lumber sugars enter the treating solution during the kickback or pressure release phase of the empty-cell cycle. The lack of precipitation is obtained by maintaining the preservative salts solution at a temperature between about 40 degrees Fahrenheit and about 70 degrees Fahrenheit; and U.S. Pat. No. 5,970,624 describes a lumber impregnation method which comprises a process to heat lumber, a process to place the heated lumbers under a vacuumed pressure, a process to immerse the heated lumbers in processing agents under the vacuumed pressure, and a process to restore the pressure of the lumbers immersed in the processing agents under the vacuumed pressure to the air pressure, and to immerse the lumbers in the processing agents under the air pressure.

Further examples include: the method of U.S. Pat. No. 5,871,817 which details immersing dry lumber in a preservative sustained by a small hydrostatic head can achieve effective impregnation; the method described in U.S. Pat. No. 6,235,403 in which in one aspect lumber is impregnated with a waterborne preservative such as CCA at elevated temperature and pressure; and the method of NZ 235036 which involves impregnating a lignocellulosic substrate to modify its physical properties (namely to increase density or harden the substrate) using traditional methods of vacuum pressure impregnation.

U.S. Pat. No. 5,871,817 describes a method which eliminates the need for large pressure and vacuum pumps. However, the plant is still complex and expensive and the process requires storage of moderate volumes of preservative chemicals. This process relies on a limited hydrostatic head to impregnate the lumber by placing the dried lumber submersed under preservative solution into a controlled depth dip tank. In such case the dried lumber at ambient temperature is submerged in a preservative solution.

As mentioned above, pre-infection of lumber with pest organisms, such as fungi, is a major problem for the lumber industry. A recent trend has been to formulate mobile biocides that have the ability to penetrate or diffuse into the substrate. Unfortunately these are often toxic and more significantly they may be readily washed from the substrate surface by rain if exposed to such immediately after application. Accordingly, other methods have been developed in attempts to effectively deliver biocide compositions to the lignocellulosic material.

Whilst modern formulations have been developed which give a degree of penetration radially into the substrate surface, this movement is not large. Since the fungi of most concern are able to grow up to 1.5 mm per day under optimum conditions it is currently necessary to treat with chemical within approximately 48 hours of exposing fresh substrate surface. In most situations this is impractical and therefore an alternative method of control or remediation is needed.

A particular difficulty in effectively treating lumber for or from pre-infection is that the lumber needs to be treated soon after felling. In this condition, the lumber contains a lot of moisture, as opposed to processed or milled lumber which will have been substantially dried. The moisture content of this type of lumber may impede the absorption of a biocide composition into it to sufficient depth to prevent or remediate growth of pest organisms, particularly fungi.

Attempts have been made to use vacuum and pressure impregnation processes (such as those described above) to force formulations into wet or saturated organic substrates to a depth which would control fungal and other pest attack. Unfortunately, ineffective penetration and excessive processing costs may result.

As mentioned previously herein, there are a number of methods of sterilisation of logs and lumber. Both hot water and steam at ambient pressure have been used to condition logs prior to conversion to veneer. Similarly steam at elevated pressure has been used commercially in poles and lumber to reduce moisture and to open pathways such as ray parenchyma such that pressure impregnation with preservatives can be facilitated. These methods however, may suffer from a number of problems.

Specific examples of methods which have been used in attempts to control pre-infection of lumber are provided below. As with the examples provided above, such methods may suffer from one or more problems.

U.S. Pat. No. 5,505,240 describes the sterilisation of debarked logs using hot water treatment. The process involves water in which the debarked logs are immersed being heated indirectly using steam coils which are submerged in the water.

U.S. Pat. No. 5,447,686 describes sterilisation of logs using steam or hot water. The process may involve the addition to the steam of a chemical comprising a biocide. This has some serious limitations in that volatile biocides must be used and which could pose severe risk to health. Additionally, in the case of hot water containing a biocide there remains a large volume of biocide containing fluid and this poses an environmental risk particularly as it will also accumulate extractives from the logs and ultimately require disposal. More serious disadvantages of this process may be difficulty in having the biocide adequately penetrate the substrate and that prevention of cracking, checking and decay is not achieved.

McLean describes the principles, processes and times required to achieve sterilisation and conditioning of substrates; MacLean, J. D. 1952. Preservative treatment of wood by pressure methods; US Department of Agriculture, Agriculture Handbook No. 40. McLean however does not anticipate the consequence of moisture loss or the need to apply subsequent prophylactic treatments.

U.S. Pat. No. 4,978,501 describes a process for sterilisation of mushroom casings using radio frequency energy. In this process casings which are typically comprised of lignocellulosic materials, are passed through an electromagnetic field. If sufficient power is applied for long enough this will result in sterilisation of the substrate. Since mushroom casings will be used immediately in relatively sterile environments there is no need to prevent re-infection.

U.S. Pat. No. 6,014,819 describes amelioration of fungal degrade by exposure of hardwood logs to steam. The process involves the moisture content of the substrate being maintained. Addition of biocides may occur during the heating process. This process may suffer from the negative features associated with the process of U.S. Pat. No. 5,447,686.

The above description and examples highlight the problems associated with known methods for treatment or impregnation of organic substrates with compositions such as preservative compositions. Problems may include one or more of: necessity to use expensive plant and processing equipment; large plant and processing equipment; extended processing and/or treatment times; excessive environmental impact; excessive energy requirements; waste of treatment composition; ineffective delivery of composition to target zones within the substrate being treated. Such problems may also exist in relation to treating organic substrates with other compositions.

OBJECT

It is an object of the present invention to provide an improved method for delivery of a composition to organic substrates, particularly lignocellulosic substrates, or at least to provide the public with a useful choice.

STATEMENT OF INVENTION

The inventor has unexpectedly discovered that effective delivery or impregnation of a composition into a substrate, such as lumber, can be achieved by using the reduced pressure (or partial vacuum) created by the rapid cooling of hot gases within the substrate when application of a cool solution to the heated substrate occurs. This method does not require pressure pumps, vacuum pumps, large pressure vessel, large chemical storage facilities or a large treatment operation. Specifically it allows use of simple and inexpensive plant with very low volumes of stored chemical.

Accordingly, in a first broad aspect, the present invention provides a method of delivering a composition to a substrate the method comprising at least the steps of:
 a) heating a target zone of a substrate; and
 b) applying a composition to a surface of the substrate comprising or immediately adjacent to the target zone; and
wherein the composition is at a temperature below that of the target zone of the substrate.

Preferably, the substrate is an organic material. More preferably, the substrate is lignocellulosic. Preferably, the lignocellulosic substrate is lumber. In one aspect, the substrate may be in need of protection or treatment to prevent or ameliorate growth of pest organisms. Alternatively, the substrate is an organic material to which certain other properties are desired to be imparted.

In one broad aspect of the invention, the lignocellulosic substrate is substantially dry. In an alternative broad aspect of the invention, the lignocellulosic substrate contains a level of moisture; for example, the substrate may be green lumber. The substrate may be freshly felled and debarked logs or freshly sawn lumber. Alternatively, the substrate is processed or milled lumber, more preferably it is high temperature kiln dried lumber.

Preferably, a target zone of the substrate is heated and held at an elevated temperature for a period prior to application of the composition.

In the instance that the lignocellulosic substrate contains a level of moisture, the method of the invention may further comprise the step of controlling loss of moisture from the target zone of the substrate during step a) or during any period within which the target zone of the substrate is held at an elevated temperature.

Preferably, the period of time the target zone of the substrate is held at an elevated temperature is a time sufficient to substantially heat to a uniform temperature, the entire target zone of the substrate. More preferably, the period is a time sufficient to sterilise at least a target zone of the substrate.

In one embodiment, the target zone of the substrate is heated to a temperature such that the temperature differential between the target zone and the composition at the time of application is 80 degrees Celsius.

Preferably, the target zone of the substrate is heated using a heating fluid. Preferably the fluid is a gas or liquid. Where liquid, the fluid is preferably hot water. Where gas, the fluid is preferably hot air or steam. Where steam, the fluid is preferably saturated steam or high pressure steam.

Alternatively, the target zone of the substrate is heated using radio frequency energy or microwave energy.

In one aspect, the pressure conditions are controlled during step a.

Preferably, the composition is a biocidal composition. Alternatively, the composition is one which may impart properties of higher density or strength to at least a target zone of the substrate. Preferably, the composition is of a polymeric or pre-polymeric nature. Preferably, the composition is an aqueous solution.

Preferably the composition is applied to the substrate by dipping, deluging, spraying, or brushing. Additionally, variations of vacuum or positive pressure impregnation may be used.

Preferably, the composition is applied as an in-line process. More preferably, the composition is applied to the substrate as part of an in-line drying process using microwave energy.

Preferably, the method is an in-line process where the substrate is heated and the substrate is sprayed or deluged in the composition.

Alternatively, the method is a batch method wherein two or more substrates are treated simultaneously.

Preferably, the composition is applied at ambient temperature.

Preferably, the composition is stable at the temperature of the substrate at the time of application.

In the case of a lignocellulosic substrate required to be treated to prevent or ameliorate growth of pest organisms, such as during pre-infection, the target zone ,preferably comprises an area from the surface of the substrate to a depth of between approximately 0.1 centimeters to approximately 4 centimeters.

In accordance with the above, in a further particularly preferred form of the invention there is provided a method of delivering a biocidal composition to a lignocellulosic substrate, the method comprising at least the steps of:
 a. heating a target zone of the lignocellulosic substrate; and b. applying a biocidal composition to a surface of the substrate comprising or immediately adjacent to the target zone;

wherein the biocidal composition is at a temperature below that of the target zone of the substrate.

In another broad aspect, the invention provides a substrate to which a composition has been delivered in accordance with a method of the invention.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

These and other aspects of the present invention, which should be considered in all its novel aspects, will become apparent from the following description, which is given by way of example only, with reference to the accompanying figures, in which.

DETAILED DESCRIPTION OF INVENTION

The following is a description of the preferred forms of the present invention given in general terms in relation to the application of the novel method. While the description focuses particularly on the delivery of compositions to lumber or logs, and more particularly focuses on delivery of biocidal compositions to remedy infection of lumber by pest organisms, it should be appreciated that the method may be equally applicable to the delivery of alternative compositions and the treatment of alternative substrates.

In general terms, the invention relates to methods of delivering a composition to a substrate, preferably an organic substrate. The method allows for absorption by, or impregnation of, the substrate by a composition without the necessity of having to apply active pressure systems.

The method of the invention may be used to deliver any fluid composition to a substrate. The composition is preferably an aqueous solution and has active components which are non-volatile at the temperature of the substrate at the time of application. Compositions of the invention may contain polar and/or non-polar solvents and the like, for example alcohol, and vegetable oils. Persons of general skill in the art to which the invention relates will no doubt appreciate various compositions that may be applicable to the invention. However, by way of example, where treatment or prevention of infection or pre-infection by pest organisms is desired, compositions (biocide or biocidal compositions) having pesticidal (fungicidal, bactericidal, insecticidal for example) or preservative properties may be used. Where it is desired that the substrate has increased density or strength properties, compositions containing certain polymeric or pre-polymeric components may be useful. Similarly, compositions may include those of use in waterproofing a substrate. Additionally, compositions containing certain dyes to colour the substrate may be used.

Whilst not wishing to be bound by any particular theory, the inventor believes that the invention works through the creation of gas filled voids in the substrate at elevated temperature into which the biocide composition (at lower temperature) is drawn following application.

As used herein, "substrate" should be taken to mean any organic material which may be in need of delivery of a composition of some nature; for example for the purposes of protection or treatment to prevent or ameliorate growth of pest organisms. Such substrate is preferably lignocellulosic, for example living trees, wood products, lumber or logs. The invention may be applicable to substrates containing a level of moisture, or those which are substantially dry.

In the case of lignocellulosic substrates, those which "contain a level of moisture" include freshly felled and debarked logs or freshly sawn lumber (so called green lumber). Those of general skill in the art to which the invention relates will be aware that freshly felled logs or freshly sawn lumber will contain approximately 150 per cent of their dry weight as moisture if softwoods and approximately 80 per cent if hardwoods.

Again, at least in the case of lignocellulosic substrates, those which are "substantially dry" include lumber dried by traditional methods. Such lumber may contain moisture of 10, approximately 5 to approximately 30 per cent as a weight proportion of the lumber dry weight. Substantially dry lignocellulosic substrates include lumber which has been processed via kiln drying and the like and may have been milled to a final, or near final product, for example a lumber composite material.

"Pests" or "pest organisms", as referred to herein, may include any organisms which may infect an organic substrate, such as wood. While the invention is particularly applicable to fungi, pest organisms may also include bacteria, insects, nematodes and the like.

When used herein, the terms "treatment" or "remediation" should be taken in their broadest possible contexts. They should not be taken to imply that a substrate is treated such that pest organisms are totally removed, although this is preferable. Prevention and amelioration of growth of pest organisms is also encompassed by the invention.

In one preferred embodiment, the method comprises at least the steps of:

a) heating a target zone of a substrate; and
b) applying a composition to a surface of the substrate comprising, or immediately adjacent, to the target zone;

wherein the composition is at a temperature below that of the target zone of the substrate.

As used herein, a "target zone" of the substrate is any zone to which it is desired to have a composition delivered. A target zone may comprise the entire substrate or any one or more parts thereof. In the case of the compositions being delivered for the purpose of treatment of infection by a pest organism, the target zone may be an area of a log which is susceptible to infection, or has been infected, by a pest organism; for example, the target zone may comprise an area from the surface of the substrate to a depth of between approximately 0.1 centimeters to approximately 4 centimeters. Persons of general skill in the art to which the invention relates will readily appreciate target zones. Target zones may become further apparent from the examples provided hereinafter.

In a particularly preferred embodiment of the invention, a target zone of the substrate is heated and held at an elevated temperature for a period prior to application of the composition.

As used herein, the "period of time" a target zone of the substrate is held at an elevated temperature is a time sufficient to substantially heat to a desired temperature, the target zone of the substrate. In a particularly preferred embodiment, the period is a time sufficient to sterilise at least a target zone of the substrate.

An "elevated temperature" is one which is higher than the temperature of the composition to be used in the method. More particularly, an elevated temperature is one sufficient to allow moisture loss from the substrate, or expansion of gases, within the substrate. In another embodiment, the temperature is sufficient to assist in sterilisation of at least a target zone of the substrate.

It should be appreciated that temperatures and times sufficient to heat and/or sterilise a target zone of a substrate may vary depending on factors such as the nature of the substrate, the means used to heat the substrate, the composition to subsequently be applied, the desired uptake and penetration of composition required and in the instance of treating a substrate against pest attack, the nature of the pests which may be present on the substrate. However, by way of example, in the case of lumber, to be sterilised using steam against growth of fungi, the inventor contemplates sterilisation times of from 20 to 150 minutes and temperatures ranging from approximately 50 to 250 degrees Celsius depending on equipment available and the depth from the surface to which sterilisation is required. Further exemplary temperatures and times are provided herein after under the heading "Examples".

It should be appreciated that use of the phrase "sufficient to sterilise" does not imply that the sterilisation process must be sufficient to completely rid the substrate of viable pest organisms. The inventor contemplates a reduction in any viable pest organisms being appropriate in respect of the invention. Additionally, there may be instances where a substrate does not actually contain viable pest organisms prior to sterilisation.

It will be appreciated that the temperature differential between target zone of the substrate and the composition at the time of its application may vary depending on the substrate to be treated and the nature of the composition to be applied. It will also be appreciated by persons of general skill in the art that the temperature differential may be adapted to control the level of penetration of composition into substrate. By way of general example, in certain cases the greater the temperature differential (to a limit), the greater the possible pressure change (as described herein after), with the possibility of greater penetration of composition into at least the target zone of the substrate. It should be appreciated that the temperature differential may be varied by varying the temperature to which a target zone of the substrate is heated, or by varying the temperature of the composition to be applied to the substrate. However, in one embodiment of the invention, the target zone of the substrate is heated to a temperature such that the temperature differential between the target zone and the composition at the time of application is approximately 80 degrees Celsius. However, the inventor contemplates higher differentials providing reduced processing time and energy savings, especially where the entire substrate is not required to be heated. Accordingly, in other embodiments, the temperature differential is greater than 80 degrees Celsius, more preferably approximately 100 degrees Celsius or greater.

The target zone of the substrate may be heated by any means suitable for doing so. In a preferred embodiment, this is done using a heating fluid, for example any gas or liquid. Where liquid, the fluid is preferably hot water. Where gas, the fluid is preferably hot air or steam. Where steam, the fluid is preferably saturated steam or high pressure steam. In one embodiment of the invention, the fluid may contain a biocide.

While the heating step may be conducted at atmospheric pressure, the invention encompasses heating at elevated pressure. Similarly, the heating step may occur under conditions which control or constrain pressure.

Alternatively, the target zone of the substrate is heated using radio frequency energy or microwave energy. In the case of radio frequency heating wavelengths of greater than 2.4 GHz are preferable. More specifically, wavelengths of approximately 27 to 40 MHz are particularly desirable. At this range of wavelength, batches of two or more separate pieces of a substrate, for example two or more logs of lumber may be treated simultaneously.

The composition may be applied to a surface of the substrate using any known means of bringing a composition into contact with a material. By way of example, the composition is applied by dipping, deluging, spraying, or brushing. While the inventor does not believe it necessary to apply active pressure to effect delivery of a composition in accordance with the invention, there may be instances where the active pressure systems (positive pressure or vacuum) may be desirable.

As mentioned herein before, the composition is applied to the substrate at a temperature below that of the target zone at the time of application. Preferably, certain temperature differentials apply, as mentioned above. While the operating temperature of the composition may vary depending on the nature of the biocide, for example its solubility and the like, the composition is preferably at ambient temperature or lower.

As mentioned hereinbefore, the method of the present invention is applicable to substrates which are substantially dry, and those which contain a level of moisture. Where the substrate contains a level of moisture, for example green lumber, the method of the invention may further comprise the step of controlling loss of moisture from the target zone of the substrate during step a) or during any period within which the target zone of the substrate is held at an elevated temperature.

Moisture loss may be controlled by manipulation of temperature, the humidity of the surrounding medium, and or the atmospheric pressure conditions. For example, a fluid medium of high humidity or a fluid medium of high pressure may be used to reduce moisture loss. Preferably the fluid is a gas or liquid. Preferably, where the fluid is a liquid, it is hot water. In the case of a gas, the gas is preferably hot air, or more preferably steam. In a particularly preferred form of the invention, the fluid medium is saturated steam or high pressure steam. In a further preferred example, the pressure conditions are constrained to prevent moisture present in the substrate from boiling. For example, the substrate may be heated using radio frequency, while simultaneously controlling pressure conditions. At a desired time and temperature the pressure constraints may be removed allowing any moisture to boil and thus be expelled from the substrate. At a time subsequent to the moisture loss, but whilst the substrate is still at elevated temperature, a composition of lower temperature is applied (for example by immersing the substrate in the composition). Such techniques are further exemplified hereinafter under the heading "Examples".

The method of the invention may be adapted to in-line processing. For example, in one embodiment, the inventor contemplates logs being heated for a controlled time in a chamber containing live steam at approximately 100 Celsius using appropriate mechanisms such as chain feeds with the logs moving progressively through the chamber. Subsequent to heating the logs may then move into a second chamber where moisture loss is controlled without substantial temperature drop. Either in that chamber or immediately subsequent the logs are dipped or deluged with preservative solution. A similar in-line process can be applied for example to microwave heated lumber wherein the lumber passes through a waveguide where it is exposed to microwave energy sufficient to raise the temperature of the substrate. Immediately upon discharge from the waveguide the lumber enters a dip tank or deluge booth where it is uniformly exposed to preservative chemical.

The processes of the invention might conveniently be combined with standard lumber planing operations. For example, after planing the lumber passes into an accumulator in which the lumber is heated. After a controlled time the lumber passes out immediately followed by a deluge spray or dip in a desirable composition. This could be described as an in-line system or continuous process and since each piece of lumber is small the required volume of preservative or chemical solution is also small. Such a system may require only 0.2 to 0.5 cubic meters of operating solution compared to a volume of 30 cubic meters for a typical operation in common use.

As an alternative to in-line processing, the invention may be applied to batch processing, which may provide an efficient and cost effective procedure. This is particularly the case where steam or radio frequency (RF) heating is employed. As mentioned herein before, where wavelengths of between, for example 27 to 40 MHz are used, a number of logs may be sufficiently heated simultaneously. Skilled persons may readily appreciate appropriate wavelengths outside this range.

As will be appreciated, as the composition is applied to the heated substrate in accordance with the method of the invention, it cools the substrate causing any gases held within the substrate (as a result of heating and moisture loss) to contract and/or condense. This creates a pressure drop and draws the composition into at least the target zone which has been heated and/or sterilised. It would be an advantage if the composition itself had properties which allowed it to penetrate the substrate to some extent (as opposed to just sitting on its surface following application); in this way, the composition may penetrate beyond the target zone. Skilled persons will readily appreciate compositions having desirable penetrative properties.

A novel feature of the invention includes the ability to use otherwise heat sensitive compositions, for example preservative solutions such as those aforementioned, like copper chrome arsenate. This is because more or less only the solution which enters the substrate will endure heating and then only for a very short time. There will be no kickback and therefore there will be no contamination or decomposition of the composition being used. Effectively each piece of lumber can be treated with virgin composition and which composition can be controlled precisely unlike previously used processes. It is envisaged that no contaminated sludge will be generated. Thus this invention may offer additional advantages over traditional processes.

EXAMPLES

The invention will now be further described with reference to the following non-limiting examples.

Example 1

Many organic substrates are susceptible to attack by pest organisms. There are recognised problems with gaining effective penetration of substrates by biocide compositions to effectively prevent or treat infection by such pests. Similarly, problems are associated with delays between collection of organic substrate material and processing to final products, including preservation steps; during this time, there is a window of opportunity for pests to attack the substrate. This may be referred to as "pre-infection" and is of particular significance in the lumber industry as is described elsewhere herein. Pre-infection by fungi is a significant problem.

The impact of fungal degrade on wood has been described by various authors. "Antisapstain Treatment of Logs and Lumber in New Zealand. Wakeling et al, 2001. Proceedings ExpoCORMA International Conference, Chile", teaches of the severity of the problem of pre-infection. In an attempt to remedy the pre-infection, people have studied new formulations designed to penetrate further into the substrate, "Sentry, a new antisapstain formulation for protecting logs and lumber, parts 1 & 2, Wakeling et al, IRG Conference 2002, Germany".

The problem is described as rapid radial growth of fungi into the substrate during the early stage from felling to processing. Whilst some staining fungi consume available carbohydrates in the form of sugars, others move rapidly through the ray parenchyma consuming triglycerides such as wood resins. Because some fungal species particularly some *Ophiostoma* are able to grow at around 1.5 millimeters per day, prevention of degrade dictates immediate processing and treatment. Whilst the more recently developed biocide compositions do penetrate somewhat into the substrate, subsequent research by the above authors and others has confirmed that with current formulating technology the window of opportunity of control can be extended to no more than 48 hours.

Due to the frequently difficult terrain and other extraction constraints, most logs felled can not be processed within this time window. Therefore the problem of pre-infection remains and still causes losses of many millions of dollars.

Attempts have been made to apply temporary prophylactic treatments at the time of felling. This is incompletely successful because the log will be damaged further after treatment allowing ingress of re-infection. Further this process is restricted to relatively flat land where mechanical harvesters are used and this comprises a small proportion of total trees felled.

Other attempts have been made to control pre-infection using various sterilisation processes. Historical methods often used steam and hot water and normally relied on long treatment times to ensure heating of the substrate throughout. In more recent times consideration has been given to use of microwave radiation because this can rapidly heat the substrate throughout.

In some circumstances heat sterilisation alone will sufficiently remediate degradation to allow lumber processing to be completed. However the sterile condition generated is temporary in that immediately upon exposure of sterilised wood to the environment it again encounters fungal spores which will re-infect the substrate. With sufficient delay in reapplying a preservative this re-infection will degrade the substrate, such as would occur with the prolonged storage and transportation times associated with shipping logs or green lumber to foreign markets.

Application of a prophylactic treatment subsequent to sterilisation will control this re-infection to some extent, but has limitations because such treatments remain on the surface of the substrate, with subsequent loss of efficacy.

In some circumstances it may not be necessary to sterilise the entire substrate. Trees are relatively self protecting when alive, after felling, cutting or bark damage however, organisms may infect the substrate from the outside in. The zone of sterilisation may be that which only includes the area which the pest, such as fungi, has penetrated since the time of felling. This may be a few millimeters to several centimeters depending on the time from felling to treatment. This is an important consideration because not only is the cost of energy critical but also shorter heating times allows higher plant throughput reducing the impact of cost of capital.

Traditional heat sterilisation causes considerable loss of moisture from the substrate with serious consequences. Drying of the substrate, which is concomitant to moisture loss, makes milling more difficult due to increased toughness of the substrate and wear on cutting edges such as saw blades. More significantly, during veneer production from logs, such peeling of drier material is more difficult, the knives used incur increased wear, and even more significantly the veneer will split resulting in a downgrade in value.

Furthermore, moisture loss may result in checking and splitting from the surface of the substrate. Such checks and splits constitute direct open pathways for ingress of biological infection at depth within the substrate. The consequences could be complete failure of the substrate.

Application of a typical fungicidal formulation by typical processes may be of limited value because the substrate is handled in a fashion prior to final use that will damage the surface and which will expose sterile but unprotected substrate to fungal attack. Because green logs are of considerable dimension and weight, very heavy duty handling equipment is required. Frequently the tines of fork lifts and loaders will bruise and/or penetrate the substrate surface to some depth, possibly as much as 2 or 3 centimeters. Any superficial treatment will be penetrated and ingress of infection will occur. This breaching of treatment also occurs with checking and splitting from subsequent drying.

Surprisingly, the inventor has found that if a substrate susceptible to attack by pests is brought to an elevated temperature while controlling moisture loss from the substrate, and substantially immediately treated with a biocide composition at a lower temperature, significant enhancement in biocide penetration into the substrate will occur.

In experiments leading to the invention, the inventor carried out studies on several heating fluids to establish the heating time and heat profile for *Pinus radiata* and other species. Recognising that the depth of sterilisation can be adjusted to meet the requirements of the extraction to processing window, that is the depth to which the fungi will have penetrated at 1.5 millimeters per day (see Table 1), measurements were made at 3 depths.

TABLE 1

| Depth (mm) | Time window (days) at 1.5 mm/day |
|---|---|
| 10 | 6.6 |
| 25 | 15.7 |
| 43 | 23.7 |

It is generally accepted that 7 to 10 days from felling to processing is achievable and therefore sterilisation of an annulus of approximately 10 mm is acceptable.

Figure 1:
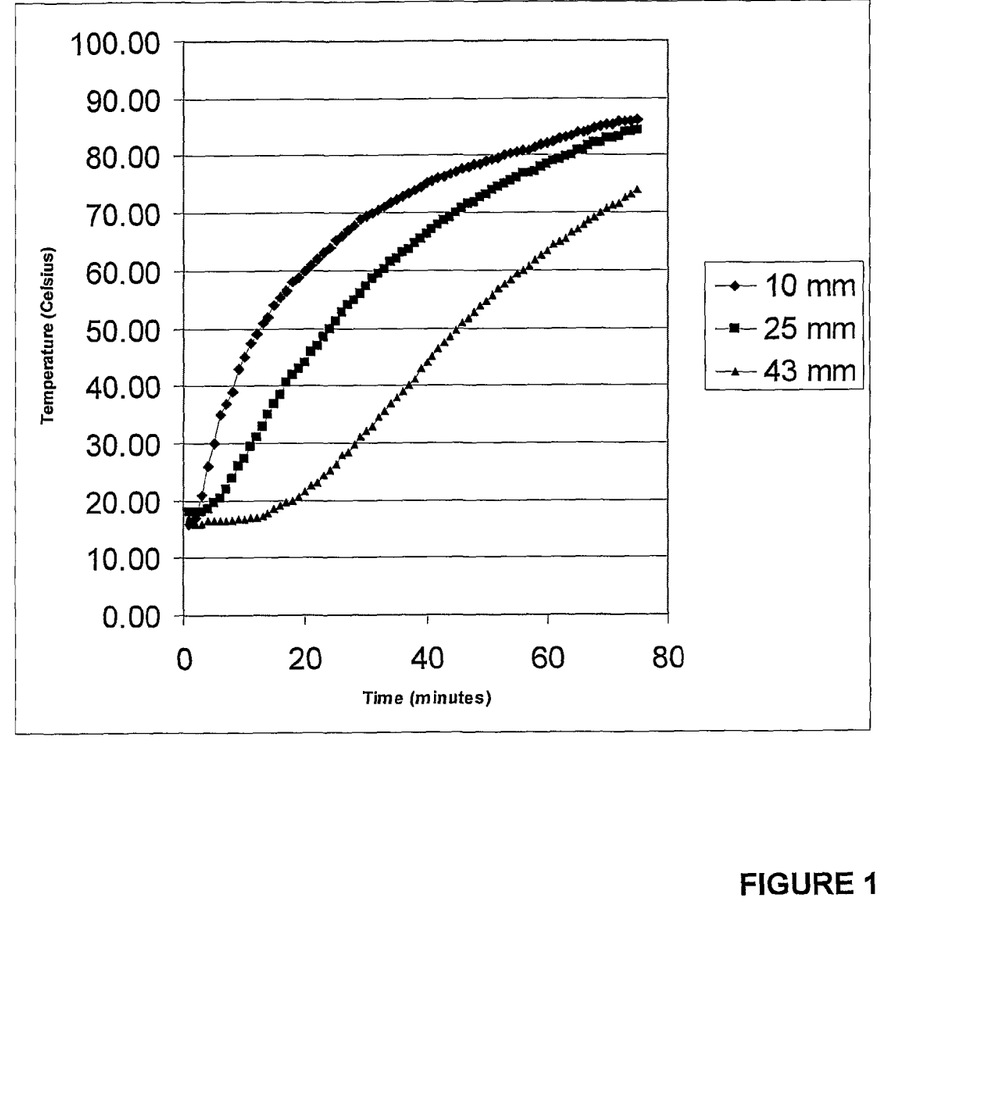
FIG. 1: Illustrates the rate of temperature change in fully water saturated log billets when exposed to live steam at 100 degrees Celsius and compares the temperature change at different depths from the log surface.

In anticipation of the need to sterilise an annulus around the substrate, temperatures were measured at various distances radially into the substrate from the surface. Times are illustrated in FIGS. 1 and 2.

Because the heating medium is able to operate at 100 per cent humidity, moisture loss during the heating step is expected to be negligible, although there may be some loss from thermal expansion of water and residual air within the substrate.

Figure 2:
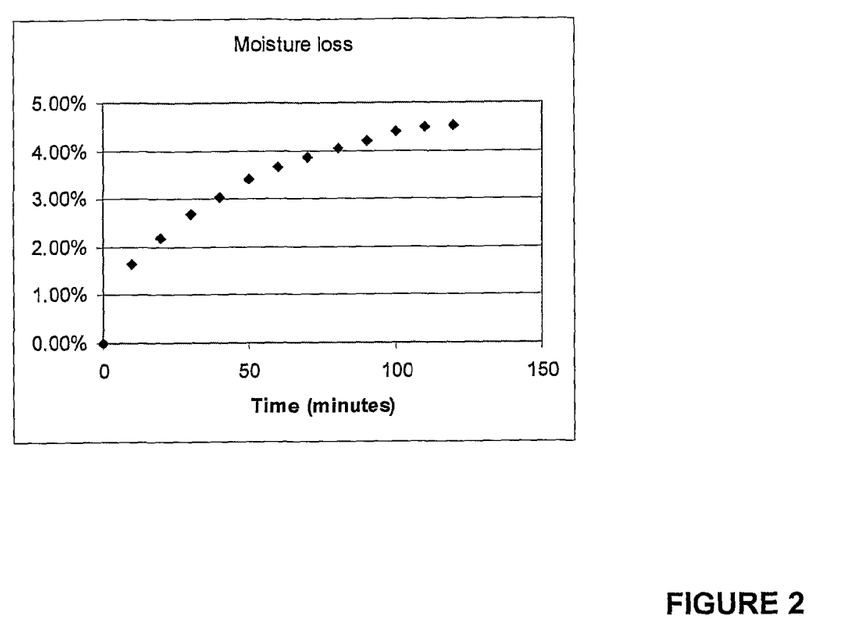
FIG. 2: Refers to FIG. 1 and illustrates the accumulated average moisture loss from the log billets with respect to time.

Although a gradual moisture loss was anticipated from the substrate subsequent to heating, the inventor found, surprisingly, that the immediate moisture loss is significant with a subsequently rapidly diminishing rate of further moisture loss (FIG. 2). The moisture loss shown in FIG. 2 is the average moisture loss in the entire substrate.

Since the loss is occurring only in the sterilised zone it can be recognised that the actual loss in that zone is the average moisture loss at a point in time multiplied by the ratio of the total area of the cross section of the log divided by the cross section area of the zone, which is the annulus treated. It can be seen that within approximately 15 to 30 minutes moisture loss can be greater than 6 per cent in the sterilised zone and that is adequate void space to either create a pressure drop by sudden cooling with biocide formulation, or for effective pressure impregnation with biocide formulation.

The inventor believes that because the zone of sterilisation is small that the moisture loss is more or less restricted to the target zone. Understanding that $$pV = nRT \text{ for a fixed mass of gas}$$

or $$\frac{P_1 V_1}{T_1} = \frac{P_2 V_2}{T_2}$$

Subsequent application of a cooler fluid reduces the pressure of the gas within the empty cells to an extent that the fluid may be drawn into the substrate. If a temperature differential of 80 Celsius is achieved this may result in a pressure differential of around 5 pounds per square inch. Since this is negative pressure it is more than adequate to draw the biocide composition into the substrate. The inventor contemplates that such movement is likely to be some distance, essentially through all void space.

Having previously developed penetrating biocide systems the inventor concluded that use of such low pressure assisted penetration of the biocide might gain further benefit due the subsequent movement of the biocide yet further into the substrate.

Broadly interpreting the results the inventor concluded that sterilisation of a zone (annulus) suitable for a felling to processing time of 7 days would require sterilisation to a depth of approximately 10 millimeters, in the case of prevention or treatment of fungal growth. In this example, since the entire zone must remain at least 56 degrees Celsius for 30 minutes the total time for sterilisation is approximately 50 minutes. Times for greater or lesser depths can be calculated according to the charts herein.

Since small moisture loss can create sufficient negative pressure with which to draw in biocide formulation the Figures provided herein illustrate that the period following sterilisation but prior to application of biocide can be selected from 0.1 minutes up to an hour or more. However since the additional moisture loss offers no great benefit and, in fact, could be a disadvantage, the time is preferably between 0.5 and 30 minutes.

The problem of biological infection occurring and developing in logs and lumber to an extent such that it cannot be readily remedied by known methods is of considerable concern to the industry. Attempts have been made to prevent the development of this infection by applying biocides to the tree during the felling process. Unfortunately due to the difficulty in gaining complete application this has limited efficacy. Further it does not overcome damage which occurs subsequent to treatment.

The present examples illustrate methods of mitigation of pre-infection in lignocellulosic substrates which comprise sterilisation of the substrate in a heating fluid during which, or subsequent to, controlled moisture loss is allowed. This creates sufficient gas filled voids in the substrate into which a biocide composition can be applied by vacuum or pressure methods.

In recognition of two critical issues relating to mitigation of pre-infection the inventor notes that the depth of sterilisation will depend on the species concerned, the time from felling to processing and the time from processing to final use. When the time from felling to treatment is relatively short it is most economical to treat a relatively shallow annulus around the substrate. This is beneficial because it reduces energy costs. The second issue of excess moisture loss is controlled by the type of heating medium, the duration of heating and the timing of the application of the fungicidal formulation and therefore in the substrate the final moisture loss may be reduced.

Further because the biocide formulation may be drawn into the substrate by controlling moisture content and temperature of the substrate this has a significant benefit because it is able to control any spores or growing fungi which may be at the limit of the sterilisation zone.

In fact there are additional commercially important benefits from this. If the biocide is applied in a fashion which encourages penetration to some depth below the surface this will protect the substrate from attack by fungi through checks, splits or regions of physical damage caused by handling. This benefit is more so when fungicides with penetrating properties are used in conjunction with this invention.

On the basis of this experimentation, the inventor learned that immediately subsequent to sterilisation gas containing voids in the substrate could be cooled creating a negative pressure which could be encouraged to take up biocide compositions in a fashion which offered a number of benefits, namely:

The biocide replaced much of the lost moisture reversing the effects of moisture loss (for example checking and splitting) which would have otherwise occurred The biocide, in replacing moisture loss, reduced the downstream effects on plant and equipment and the damage which would otherwise occur to the likes of veneers produced from the substrate By being drawn substantially into the substrate the biocide is able to prevent re-infection both on the surface and more particularly in areas where checking, splitting or mechanical damage would otherwise expose sterile but unprotected substrate Further, the inventor is aware that current biocide technology can not provide sufficient efficacy for logs which are more than 48 hours from felling. However, if the pre-infected annulus is completely sterilised by the process of this invention the effective time from felling may be returned to zero, that is the sterile condition as existed in the original tree.

The inventor has concluded that a process or method described herein may offer a practical and inexpensive alternative which can remedy pre-infection in logs and green lumber and which may significantly reduce the value otherwise lost to the downgrade of these materials due to disfigurement or decay.

The enhanced penetration observed by the inventor is believed to have both commercial and environmental consequences. If the preservative formulation has enhanced control of wood degrading organisms this might allow a reduced loading of chemical in the treated substrate without loss of performance. This may be achieved by using less concentrated biocide solutions which has an environmental benefit. The lower rate of application also allows a reduction in the cost of treatment.

Example 2

Using the principles applied in relation to the above examples, the inventor set out to study whether the invention was applicable to lumber which was substantially dry. The inventor obtained samples of Monterey pine (*Pinus radiata*) and Baltic pine (*Pinus sylvestrus*) which is very similar to Ponderosa pine (*Pinus ponderosa*). Some of these samples were high temperature kiln dried by traditional methods and some were dried using conventional air drying known to those versed in the art of lumber drying.

The samples were flat sawn, that is the growth rings were parallel to the wide face of the samples. The sample dimensions were 100 mm by 50 mm by 150 mm in length. 100 mm by 50 mm is the typical cross section lumber used in house frame and for other purposes.

Duplicate studies used samples which were finished by planing the surface; others were left in rough sawn state.

In all cases control samples were also included in the study but wherein the heating step was omitted.

Example 2A

High temperature kiln dried lumber samples were heated to 100 Celsius for 30 minutes in hot air. Subsequent to heating the samples were immediately quenched in an aqueous acidic copper containing preservative solution and were left in the solution for 2 minutes. Such solution was at ambient temperature.

A copper containing preservative was selected because solutions of this metal are commonly used as lumber preservatives and also because it is a simple process to determine distribution of the preservative within the substrate by use of a simple colour change spot test. In these studies pyridyl azo naphthol was used as the spot test reagent because it is a sensitive detector of copper.

Subsequent to treatment the samples were allowed to dry. They were then sectioned parallel to the face and spot tested with pyridyl azo naphthol dissolved in ethanol. The entire exposed face turned dark crimson red indicative of the presence of copper and which indicates complete distribution of the preservative.

The results of this study using the above detection method showed that complete penetration and distribution throughout the lumber samples could be achieved.

Example 2B

High temperature kiln lumber samples were heated to 150 Celsius for 30 minutes in hot air. Subsequent to heating the samples were immediately quenched in an aqueous acidic copper containing preservative solution and were left in the solution for 2 minutes. Such solution was at ambient temperature.

Subsequent to treatment the samples were allowed to dry. They were then sectioned parallel to the face and spot tested with pyridyl azo naphthol dissolved in ethanol.

The results of this study using the above detection method showed that complete penetration and distribution throughout the lumber samples could be achieved.

Example 2C

Air dried lumber samples were heated to 150 Celsius for 30 minutes in hot air. Subsequent to heating the samples were immediately quenched in an aqueous acidic copper containing preservative solution and were left in the solution for 1 minute. Such solution was at ambient temperature.

Subsequent to treatment the samples were allowed to dry. They were then sectioned parallel to the face and spot tested with pyridyl azo naphthol dissolved in ethanol.

The results of this study using the above detection method showed that complete penetration and distribution throughout the lumber samples could be achieved.

Example 2D

Air dried lumber samples were heated in a conventional kitchen microwave oven operating at 900 watts for 60 seconds. Subsequent to heating the samples were immediately quenched in an aqueous acidic copper containing preservative solution and were left in the solution for 1 minute. Such solution was at ambient temperature.

Subsequent to treatment the samples were allowed to dry. They were then sectioned parallel to the face and spot tested with pyridyl azo naphthol dissolved in ethanol.

Results were as for example 2A.

The same preservative solution was used for all the above examples such that any changes in appearance or composition could be noted. During the process and subsequently 5 days later the composition remained clear and of consistent composition.

As noted previously herein, some known methods of biocide treatment necessitate uptake of fluids into dried lumber as high as 700 liters per cubic meter. In the above studies uptakes ranged from 50 liters to 100 liters depending on the temperature generated within the substrate and the length of exposure of the heated substrate to the application fluid.

Conveniently the composition or strength of the compositions used can be adjusted in strength to achieve the various requirements of the final use of such substrates.

The results of this study using the above detection method showed that complete penetration and distribution throughout the lumber samples could be achieved.

Thus the inventor learned that immediately subsequent to heating, gas filled voids in the substrate could be encouraged to take up preservative or other chemical compositions by the cooling actions of the preservative or other chemical compositions in a fashion which offered a number of benefits namely;

- The preservative or other chemical composition uptake is significantly lower than that normally associated with vacuum/pressure impregnation of lumber
- The preservative or other chemical composition can be applied by simple inexpensive plant and equipment without recourse to vacuum and pressure processes
- The preservative or other chemical composition may be created as required thus minimising the total volume required and thus minimising potential impact on workers or the environment.

Example 3

This example relates to a process wherein the substrate is constrained in a chamber above atmospheric pressure and the substrate heated using radio frequency energy.

Example 3A

Green lumber is placed in an autoclave and the doors closed. An over pressure within the autoclave of 30 pounds per square inch is applied. The increased pressure is applied using any gas and is most economically air. Energy is then applied in the form of radio frequency energy, preferably at a frequency below 100 MHz, and more preferably at a pressure of between 27 to 40 MHz. This allows immediate heating of the substrate, without need for venting or a slow heat up. In addition, no condensate is created in this process because no live steam is applied and because any water within the substrate is constrained due to pressure conditions. After a time when sufficient energy has been applied to achieve the desired temperature throughout the substrate (or example 130 degrees Celsius), the pressure is rapidly released whereupon water within the substrate will boil causing evaporative loss and also generating internal pressure which causes mass flow of free wood moisture and clears the substrate of certain cellular structures and debris. After allowing controlled moisture loss, preferably with minimal temperature loss, the vessel is flooded with preservative fluid at a temperature lower than that of the substrate. Fluid is drawn into the substrate. The vessel is then drained of surplus fluid and the treated substrate removed. Additional use of pressure or vacuum sequences may be used but are not essential to the process.

Example 3B

Green lumber is placed in an autoclave which is then hermetically sealed. Energy is applied in the form of radio frequency energy, preferably at a frequency below 100 MHz and more preferably at a wavelength of between 27 to 40 MHz. This creates an increase in pressure within the autoclave due to steam generated by heating of the substrate and thermal expansion of air in the autoclave. Some condensate is created during pressure development but is minimal compared to conventional steaming or kiln conditioning. Continuation of the process is then similar to and subject to the same variations as Example 3A.

Subsequent to removal from the vessel (after the processes of Example 3A and 3B above) the treated substrate may still retain some energy. This may benefit the drying of the substrate and the fixation of the preservative within the substrate.

Example 4

In many countries it is a requirement to treat less durable wood species with preservatives to prevent attack by insects or wood degrading fungi. Also it is frequently required that lumber used for framing, joinery and other purposes by kiln dried to eliminate distortion. These two requirements are normally incompatible because dried lumber when treated with the likes of water based preservatives will again become wet, thus necessitating re-drying which is costly. Further it is impractical to use some common preservatives such as boron salts because these migrate out of the wood again during re-drying.

The final moisture content required of purveyors of treated lumber is around 15% -20% based on the dry weight of the lumber. This amounts to around 70 kilograms of water per cubic meter for lumber with a basic density of 440 kilograms per cubic meter. Frequently the lumber is dried substantially below this moisture content and is either reconditioned or is allowed to re-equilibrate to the desired moisture content.

Alternatively, a process known as LOSP is prescribed wherein the preservative material is dissolved in a Light Organic Solvent which is impregnated into the already dry lumber. This process is very expensive and liberates copious volatile organic compounds from the lumber into the atmosphere subsequent to treatment. These solvents are flammable and this creates another hazard.

One aspect of the present invention relates to the treatment of already dry lumber with moisture content of approximately 15% or below. During processing the moisture content of such wood is further reduced. Upon treatment of the lumber according to the present invention the moisture content will increase but will not exceed the range required by the purveyor.

For example, in New Zealand it is a requirement that lumber used for framing of buildings be treated to a specific standard. That standard allows use of boron salts with a required retention of 0.4% as boric acid based on the dry weight of lumber. Treatment by traditional vacuum pressure impregnation techniques necessitates application of more than 100 liters of aqueous solution per cubic meter. Even if the lumber were absolutely dry prior to treatment the final moisture content would exceed the standard required because 100 liters of moisture contributes 23 per cent moisture content.

Using the process of our invention one can achieve low liquid retentions and yet apply adequate preservative, as is demonstrated by this example.

Kiln dried *Pinus radiata* lumber samples of dimensions 100 mm×50 mm by 150 mm length were prepared in a laboratory. The initial moisture content was 7%. The ends were sealed with two applications of a surface coating to prevent end effects during the impregnation process.

The samples were heated in a conventional microwave oven for various times at various power levels, held for controlled periods to allow temperature equilibration, and then submerged for various times in an aqueous preservative containing boron salts.

A large range of data were generated with a selection listed in Table 2 below.

TABLE 2

| Sample | Power (watts) | Heating time (seconds) | Stand time (seconds) | Dip time (seconds) | Uptake (L/m3) |
|---|---|---|---|---|---|
| 1 | 400 | 30 | 15 | 120 | 10.53 |
| 2 | 400 | 60 | 15 | 120 | 21.42 |
| 3 | 400 | 90 | 30 | 120 | 26.78 |
| 4 | 200 | 70 | 15 | 120 | 12.19 |
| 5 | 200 | 150 | 15 | 120 | 25.04 |
| 6 | 200 | 140 | 20 | 180 | 22.66 |
| 7 | 200 | 120 | 15 | 180 | 17.69 |

In the above cases the fluid was an aqueous solution containing boric acid at 10% by weight. All of the samples with an uptake greater than 17.6 liters per cubic meter exceed the required boric acid retention.

The above data is a limited set of the work carried out. We have found that uptake achieved by the process is a function of the energy input, the delay between heating and exposure to the preservative fluid, and the extent of exposure to that fluid.

For example, multiple linear regression analysis applied to a large set of data indicated the following relationship:

Uptake, $L/m^3$=4.24×Energy−0.0145×Stand Time+ 0.0555×Dip Time−5.21 where Energy was in kWh, and Stand Time and Dip Time were in seconds.

For this data set the value of $R^2$ was 0.687 and standard error was 5.66L/$m^3$. This analysis showed that stages of the process could be customized to target a desired absorption.

Example 5

A group of mini packets of high temperature kiln dried *Pinus radiata* were assembled each from 12 individual boards of material of width 100 mm and thickness 50 mm. These mini packets of lumber were exposed to RF energy of 1000 watts for 30 minutes sufficient to apply 100 kilowatt seconds of energy per kilogram of substrate. Each mini packet was then immediately immersed in a fluid containing 15 per cent boric acid solution. The measured uptake of fluid was 30 liters per cubic meter. Two hours subsequently the moisture had in part evaporated giving a final equivalent moisture uptake of 20 liters per cubic meter.

Each sample piece was cut in cross section 1 week later and spot tested with curcumin. The spot tests indicated that the boron fluid had penetrated into the core of practically all samples. Similar lumber samples dipped in the same solution without prior RF energy treatment had a very narrow annulus of penetration of approximately 1 mm around all surfaces.

Re-treatment of kiln dried lumber with waterborne solutions has always been very difficult because known processes always resulted in high uptakes. This then resulted in substantial change to overall moisture content and to dimensional stability. The inventor has surprisingly found that final moisture content resulting from the process of this invention resulted in a minor change of around 4 per cent on wood weight. More surprisingly the dimensional change was less than 0.5 per cent change in width and less than 1 per cent change in thickness. This is within normal production tolerance.

In this embodiment of the invention the inventor has achieved a very low uptake using waterborne solutions yet have treated the lumber samples adequately.

It should be noted that with a method of the invention (whether in relation to green or dry substrate) the final uptake of composition most preferably includes a fluid volume which replaces any moisture loss which may occur during the period of energy application and stand time before fluid application, in addition to the net fluid gain which is apparent between start and finish of the method. While this component is more significant when the process is applied to green or wet substrate it may also be an important aspect for dry substrate, in that the process may be manipulated to increase total fluid uptake without significantly increasing net change in moisture content. This is particularly important where dimensional change associated by swelling from carrier absorption is to be minimized. Of course, it will be appreciated that there may be instances where maintenance or manipulation of moisture content of the substrate is not critical or important.

The inventor has concluded that a process or method described herein can offer a practical and inexpensive alternative to impregnate porous substrates, more particularly lumber, and which can significantly reduce the cost of capital plant otherwise associated with such methods.

Surprisingly, by using a process of the present invention, the inventor found a significant enhancement in biocide penetration into lignocellulosic substrates without recourse to vacuum or pressure methods. The enhanced penetration observed by the inventor is believed to have both commercial and environmental consequences. If the preservative or chemical composition is able to impregnate the substrate without recourse to vacuum and pressure pumps plant and the cost thereof is significantly reduced. This might be achieved by using lower volumes of preservative or chemical compositions and this has an environmental benefit because of reduced risk of spill or loss into the environment.

A further advantage of the present method where the treating solution is maintained at a low volume and is prepared as required is that there will be little recycle. Accordingly, there will be minimal problems, if not none of the problems, that may be encountered with recycle in large treatment plants.

The invention has been described herein, with reference to certain preferred embodiments, in order to enable the reader to practice the invention without undue experimentation. However, a person having an ordinary or general skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the field of endeavour to which the invention relates in New Zealand or any other country.

Throughout this specification, unless the context requires otherwise, the words "comprise", "comprising" and the like, are to be construed in an inclusive sense as opposed to an exclusive sense, that is to say, in the sense of "including, but not limited to".

The invention claimed is:

1. A method of delivering an aqueous composition to a kiln dried lignocellulosic substrate the method comprising at least the steps of:
   a) heating a target zone of the substrate using radio frequency energy or microwave energy, and
   b) applying the composition to a surface of the substrate comprising or immediately adjacent to the heated target zone wherein the composition is at a temperature below that of the heated target zone at the time the composition is applied, the difference between the temperatures of the composition and the heated target zone being sufficient to reduce pressure in the substrate after the composition is applied, allowing for an uptake of less than 100 l/m³ of the composition into the substrate.

2. A method as claimed in claim 1, wherein the kiln dried substrate has an initial moisture content of less than 15%.

3. A method as claimed in claim 1, wherein the substrate is lumber.

4. A method as claimed in claim 1, wherein the frequency of the radio frequency energy is approximately 100 MHz or below.

5. A method as claimed in claim 4 wherein the frequency of the radio frequency energy is from approximately 27 MHz to approximately 40 MHz.

6. A method as claimed in claim 1, wherein the target zone of the substrate is heated to a temperature such that there is a temperature differential of at least approximately 80 degrees Celsius between the target zone and the composition at the time of application.

7. A method as claimed in claim 6, wherein the temperature differential is at least approximately 100 degrees Celsius.

8. A method as claimed in claim 1, wherein the composition is applied at ambient temperature.

9. A method as claimed in claim 1, wherein the target zone comprises a volume of the substrate including an area of the surface of the substrate to a depth of between approximately 0.1 cm and approximately 4 cm.

10. A method as claimed in claim 1, wherein the target zone of the substrate is heated and held at an elevated temperature for a period of time prior to application of the composition.

11. A method as claimed in claim 10, wherein the substrate is held at an elevated temperature for a period of time sufficient to heat substantially the whole target zone to a substantially uniform temperature.

12. A method as claimed in claim 10, wherein the period is a time sufficient to sterilize at least the target zone of the substrate.

13. A method as claimed in claim 1, wherein the method further comprises the step of controlling loss of moisture from the target zone of the substrate during step a) or during any period prior to step b) within which the target zone of the substrate is held at an elevated temperature.

14. A method as claimed in claim 1, wherein the composition is a biocidal composition, is a composition that imparts properties of higher density or strength to at least a target zone of the substrate or a waterproofing composition.

15. A method as claimed in claim 14, wherein the composition is of a polymeric or pre-polymeric nature.

16. A method as claimed in claim 1, wherein the composition is applied to the substrate by one or more of dipping, deluging, spraying, or brushing.

17. A method of delivering an aqueous composition to a lignocellulosic substrate the method comprising at least the steps of:
   a) heating a target zone of the substrate using radio frequency energy or microwave energy, and
   b) applying the composition to a surface of the substrate comprising or immediately adjacent to the heated target zone; wherein the lignocellulosic substrate has a moisture content of less than 15% as a weight proportion of dry weight prior to the heating step and the composition is at a temperature below that of the heated target zone at the time the composition is applied, the difference between the temperatures of the composition and the heated target zone being sufficient to reduce pressure in the substrate after the composition is applied, allowing for an uptake of less than 100 l/m³ of the composition into the substrate.

18. A method as claimed in claim 17, wherein the substrate is lumber.

19. A method as claimed in claim 17, wherein the frequency of the radio frequency energy is approximately 100 MHz or below.

20. A method as claimed in claim 19, wherein the frequency of the radio frequency energy is from approximately 27 MHz to approximately 40 MHz.

21. A method as claimed in claim 17, wherein the target zone of the substrate is heated to a temperature such that there is a temperature differential of at least approximately 80 degrees Celsius between the target zone and the composition at the time of application.

22. A method as claimed in claim 21, wherein the temperature differential is at least approximately 100 degrees Celsius.

23. A method as claimed in claim 17, wherein the composition is applied at ambient temperature.

24. A method as claimed in claim 17, wherein the target zone comprises a volume of the substrate including an area of the surface of the substrate to a depth of between approximately 0.1 cm and approximately 4 cm.

25. A method as claimed in claim 17, wherein the target zone of the substrate is heated and held at an elevated temperature for a period of time prior to application of the composition.

26. A method as claimed in claim 25, wherein the substrate is held at an elevated temperature for a period of time sufficient to heat substantially the whole target zone to a substantially uniform temperature.

27. A method as claimed in claim 25, wherein the period is a time sufficient to sterilize at least the target one of the substrate.

28. A method as claimed in claim 17, wherein the method further comprises the step o controlling loss of moisture from the target zone of the substrate during step a) or during any period prior to step b) within which the target zone of the substrate is held at an elevated temperature.

29. A method as claimed in claim 17, wherein the composition is a biocidal composition, a composition that imparts properties of higher density or strength to at least a target zone of the substrate, or a waterproofing composition.

30. A method as claimed in claim 29, wherein the composition is of a polymeric or pre-polymeric nature.

31. A method as claimed in claim 17, wherein the composition is applied to the substrate by one or more of dipping, deluging, spraying, or brushing.

* * * * *